United States Patent
Lee et al.

(10) Patent No.: US 7,112,630 B2
(45) Date of Patent: Sep. 26, 2006

(54) WATER-SOLUBLE, ANTIMICROBIAL ACTIVE POLYMER AND INK COMPOSITION COMPRISING THE SAME

(75) Inventors: Kyung-hoon Lee, Gyeonggi-do (KR); Seung Min Ryu, Gyeonggi-do (KR); Yeon-kyoung Jung, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 410 days.

(21) Appl. No.: 10/647,144

(22) Filed: Aug. 25, 2003

(65) Prior Publication Data

US 2004/0106698 A1 Jun. 3, 2004

(30) Foreign Application Priority Data

Aug. 28, 2002 (KR) .................... 10-2002-0051157

(51) Int. Cl.
*C08F 8/00* (2006.01)
*C08G 63/91* (2006.01)
*C08G 77/14* (2006.01)
*C08G 77/26* (2006.01)
*C08G 77/42* (2006.01)
*C09D 11/10* (2006.01)
*C08L 29/04* (2006.01)

(52) U.S. Cl. .................... 525/61; 528/29; 528/38; 523/122; 523/160; 524/557

(58) Field of Classification Search ................ 523/160, 523/161

See application file for complete search history.

(56) References Cited

U.S. PATENT DOCUMENTS

| | | | | |
|---|---|---|---|---|
| 2,928,858 | A | * 3/1960 | Morehouse | .................. 556/419 |
| 5,085,698 | A | * 2/1992 | Ma et al. | ..................... 524/388 |
| 6,059,869 | A | * 5/2000 | Fassler et al. | ........... 106/31.27 |
| 2004/0011248 | A1 | * 1/2004 | Taguchi et al. | .......... 106/31.28 |

* cited by examiner

*Primary Examiner*—Callie Shosho
(74) *Attorney, Agent, or Firm*—Staas & Halsey LLP

(57) ABSTRACT

A water-soluble, antimicrobial active polymer and an ink composition are prepared by coupling an antimicrobial active compound to a branch of polyvinylalcohol. An excellent antimicrobial effect is provided without affecting the properties of the ink composition that includes the polymer. The polymer is added to the ink composition in an amount of 1 to 10 parts by weight based on 100 parts by weight of the ink composition. The ink composition provides extended storage stability due to no coagulation, effective antimicrobial effect even in a printed picture, and no irritation to human skin.

21 Claims, No Drawings

WATER-SOLUBLE, ANTIMICROBIAL ACTIVE POLYMER AND INK COMPOSITION COMPRISING THE SAME

CROSS-REFERENCE TO RELATED APPLICATIONS

This application claims the priority of Korean Patent Application No. 2002-51157, filed on Aug. 28, 2002, in the Korean Intellectual Property Office, the disclosure of which is incorporated herein in its entirety by reference.

BACKGROUND OF THE INVENTION

1. Field of the Invention

The present invention relates to a water-soluble, antimicrobial active polymer, and more particularly, to a water-soluble polymer with antimicrobial activity, resulting from introducing an antimicrobial active compound into a water-soluble polymer. The present invention also relates to an ink composition comprising the water-soluble, antimicrobial active polymer.

2. Description of the Related Art

Generally, antimicrobial agents are applied to products that have frequent contact with water such as fibers, shoes, sponge gourds, and medical goods. Such antimicrobial agents are designed to have washing resistance or water-insoluble characteristic in order to maintain antimicrobial effects. For this reason, such antimicrobial agents had not been applied to water-soluble ink compositions.

Ink compositions comprise a colorant, a solvent and an additive. When stored for a long duration, ink properties and storage stability of ink compositions deteriorate due to reproduction and growth of bacteria in the ink. For this reason, an antimicrobial agent is separately added to ink compositions. Conventionally, organic compounds such as 1,2-benzisothiazolin-3-one (BIT) and methyl 2-benzimidazole carbamate (Carbendazim) are widely used as antimicrobial and preserving agents. They are separately added to ink compositions in an amount of 0.05–0.5% by weight for the purpose of extended storage duration. However, a nozzle is easily clogged due to ink coagulation and the homogeneity of ink droplets cannot be easily secured. Furthermore, when human skin is in contact with such ink compositions, skin irritation may occur. Therefore, handling property is deteriorated. Meanwhile, in case of using another antimicrobial agents with lower antimicrobial activity to overcome these problems, extended storage stability is decreased. Furthermore, it is difficult to select dyes or pigments which are well compatible with such antimicrobial agents. As a result, an optimal color quality cannot be easily accomplished.

SUMMARY OF THE INVENTION

Additional aspects and advantages of the invention will be set forth in part in the description which follows and, in part, will be obvious from the description, or may be learned by practice of the invention.

An embodiment of the present invention provides a water-soluble polymer with excellent antimicrobial activity and storage stability. When added to an ink composition, the water-soluble polymer does not adversely affect physical properties of the ink composition.

An embodiment of the present invention also provides an ink composition comprising the water-soluble polymer.

In accordance with an aspect of the present invention, a water-soluble, antimicrobial active polymer represented by the Formula 1 is used:

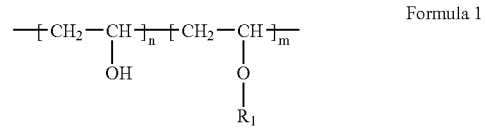

Formula 1 wherein:
n and m are the number of repeated units, n is 0.7–0.95 and m is 0.05–0.3, provided that n+m=1; and
$R_1$ is a silane derivative represented by the Formula 2:

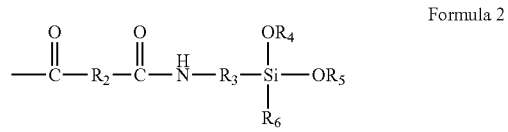

Formula 2 wherein:
$R_2$ is selected from the group consisting of an alkylene of 1–30 carbon atoms, heteroalkylene of 1–30 carbon atoms, an arylene of 6–20 carbon atoms, an arylalkylene of 6–20 carbon atoms, a heteroarylene of 6–30 carbon atoms, and a heteroarylalkylene of 6–30 carbon atoms, each of which is unsubstituted or substituted with a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 1–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms;
$R_3$ is selected from the group consisting of an alkylene of 1–12 carbon atoms, an alkenylene or an alkynylene of 2–12 carbon atom, and a heteroalkylene of 1–12 carbon atoms, each of which is unsubstituted or substituted with a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms;
$R_4$ and $R_5$ are independently one of hydrogen, and an alkyl of 1–5 carbon atoms; and
$R_6$ is one of a hydrogen, a hydroxyl, and an alkoxyl of 1–5 carbon atoms.

According to specific embodiments of the present invention, the silane derivative of the Formula 2 may be a compound represented by the Formula 3:

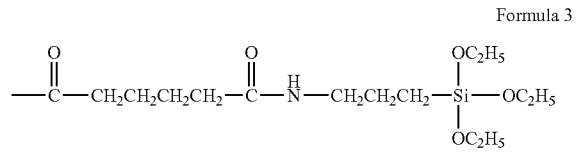

Formula 3

The silane derivative of the Formula 2 may be a compound represented by the Formula 4:

Formula 4:

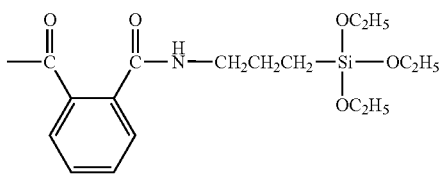

The silane derivative of the Formula 2 may be a compound represented by the Formula 5:

Formula 5

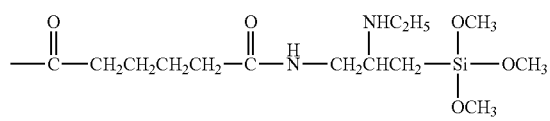

The silane derivative of the Formula 2 is a compound represented by the Formula 6:

Formula 6

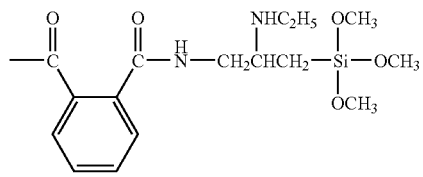

According to another aspect of the present invention, an ink composition comprises the water-soluble, antimicrobial active polymer of the present invention in an amount of 1 to 10 parts by weight.

DETAILED DESCRIPTION OF THE PREFERRED EMBODIMENTS

Reference will now be made in detail to the present preferred embodiments of the present invention.

The water-soluble, antimicrobial active polymer of the present invention is obtained by introducing a silane derivative with excellent antimicrobial activity into a branch of a polyvinylalcohol which is used as a wetting agent or a thickening agent in a water-soluble ink. Unlike a conventional antimicrobial agent which is separately added to an ink composition, the water-soluble, antimicrobial active polymer is added to an ink composition as a moiety of the polyvinylalcohol. Therefore, the water-soluble, antimicrobial active polymer provides a water-soluble ink with excellent antimicrobial activity without affecting the properties of a water-soluble ink.

The silane derivative of the Formula 2 has at least two hydroxyl or alkoxyl groups. It can be obtained via the formation of an amide bond between a dicarboxylic acid and 3-aminopropyltriethoxysilane, 3-aminopropyltrihydroxysilane, 3-(2-aminoethyl)aminopropyltrihydroxysilane, or 3-(2-aminoethyl)aminopropyltriethoxysilane. The dicarboxylic acid as used herein has a substituted or unsubstituted alkylene of 1–30 carbon atoms, a substituted or unsubstituted heteroalkylene of 1–30 carbon atoms, a substituted or unsubstituted arylene of 6–20 carbon atoms, a substituted or unsubstituted arylalkylene of 6 to 30 carbon atoms, a substituted or unsubstituted heteroarylene of 6–30 carbon atoms or a substituted or unsubstituted heteroarylalkylene of 6–30 carbon atoms.

The water-soluble, antimicrobial active polymer of an embodiment of the present invention is obtained by reacting polyvinylalcohol with the antimicrobial active silane derivative of the Formula 2. As a result, the antimicrobial active silane derivative is introduced into a branch of the polyvinylalcohol. The silane derivative as used herein is generally used as an antimicrobial agent, a wetting agent and a surfactant. It is mainly used as a surface cleaning solution. In particular, it is known to have an excellent antimicrobial activity.

The term, "alkylene" as used herein refers to a straight or branched chain group of 1–30 carbon atoms, preferably a straight or branched chain group of 1–20 carbon atoms, and more preferably a straight or branched chain group of 1–12 carbon atoms. Examples of the alkylene include methylene, ethylene, n-propylene, isopropylene, n-butylene, isobutylene, sec-butylene, t-butylene, pentylene, isoamylene, hexylene, heptylene, octylene, nonylene, decylene and dodecylene. One or more hydrogen atoms on the alkylene may be substituted by a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms.

The term, "alkenylene" or "alkynylene" as used herein refers to a straight or branched chain group containing a carbon-carbon double bond or triple bond in a central portion or at one end of the alkylene as defined in the above. Examples of such groups include ethenylene, propenylene, butenylene, hexenylene and ethynylene.

The term, "heteroalkylene" as used herein refers to a straight or branched chain group containing nitrogen, sulfur, oxygen or phosphorus in the alkylene as defined above. Examples of the heteroalkylene include methylenoxy, ethylenoxy, propylenoxy, butylenoxy and t-butylenoxy. Examples of the heteroalkylene having a substituted group include a haloalkylenoxy compound such as fluoromethylenoxy, chloromethylenoxy, trifluoromethylenoxy, trifluoroethylenoxy, fluoroethylenoxy and fluoropropylenoxy. One or more hydrogen atoms on the heteroalkylene may be substituted by a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms.

The term, "arylene" as used herein, which is used alone or in combination, refers to an aromatic compound of 6–20 carbon atoms containing one or more rings. The rings may be attached to each other as a pendant group or may be fused. The arylene is an aromatic compound such as phenylene, naphthylene, tetrahydronaphthylene and biphenylene. Preferably, arylene is phenylene or naphthylene. The arylene may have a substituent such as hydroxyl, halo, haloalkyl, nitro, cyano, alkoxy and lower alkylamiNo. One or more hydrogen atoms on the arylene may be substituted by a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms.

The term, "arylalkylene" as used herein refers to a lower alkylene, for example methylene, ethylene and propylene appended to the arylene as defined in the above. Examples of the arylalkylene include phenylmethylene and phenylethylene. One or more hydrogen atoms on the arylalkylene may be substituted by a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms.

The term, "heteroarylene" as used herein refers to a monovalent monocyclic or bicyclic aromatic compound of 6–30 carbon atoms containing one, two or three hetero atoms selected from N, O, P or S. Examples of the heteroarylene include, but are not limited to, thienylene, benzothienylene, pyridylene, pyrazinylene, pyrimidinylene, pyridazinylene, quinolinylene, quinoxalinylene, imidazolylene, furanylene, benzofuranylene, thiazolylene, isoxazolylene, benzisoxazolylene, benzimidazolylene, triazolylene, pyrazolylene, pyrolylene, indolylene, 2-pyridonylene, 4-pyridonylene, N-alkyl-2-pyridonylene, pyrazynonylene, pyridazynonylene, pyrimidinonylene, oxazolonylene, and N-oxide thereof (for example, pyridylene N-oxide, quinolynylene N-oxide) and quaternary salt thereof. One or more hydrogen atoms on the heteroarylene may be substituted by a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or heteroarylalkyl of 6–30 carbon atoms.

The term, "heteroarylalkylene" as used herein refers to a lower alkylene group, for example methylene, ethylene and propylene appended to the heteroarylene as defined in the above. One or more hydrogen atoms on the heteroarylalkylene may be substituted by a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms.

The ink composition of the present invention comprises the water-soluble, antimicrobial active polymer of 1 to 10 parts by weight based on 100 parts by weight of the ink composition. If the content of the polymer is 1 part by weight or less, desired antimicrobial effect cannot be accomplished. On the other hand, if the content of the polymer exceeds 10 parts by weight, the properties of the ink composition are adversely affected.

The ink composition of an embodiment of the present invention comprises a colorant, an aqueous medium, and a dispersing agent. Generally, polyvinylalcohol is used as a dispersing agent. The water-soluble polymer of the present invention acts as an antimicrobial agent in addition to as a dispersing agent. The ink composition may further comprise one or more dispersing agents (referred to as "secondary dispersing agent", hereinafter) except for the polyvinylalcohol to secure dispersibility or storage stability of the colorant. Although there are no particular limitations on the secondary dispersing agent, it is preferable to use dispersing agents with simple structure and low molecular weight in terms of physical properties and storage stability of the ink composition. Examples of the secondary dispersing agent include, but are not limited to, polyvinylalcohol (PVA), cellulosics, ethylene oxide modified phenol, ethylene oxide/propylene oxide polymer, a sodium polyacrylate solution (TEGO, disperse 715W), a modified polyacryl resin solution (TEGO, disperse 735W), solution of an alkylol ammonium salt of a low molecular weight polycarboxylic acid polymer (BYK-Chemie, Disperbyk), solution of an alkylol ammonium salt of polyfunctional polymer (BYK-Chemie, Disperbyk-181) or a mixture thereof. A high molecular weight dispersing agent such as a block copolymer may also be used.

In the ink composition of an embodiment of the present invention, an aqueous medium is used as a solvent. The aqueous medium is water alone or water in combination with one or more organic solvents. The organic solvent is present in an amount of 5 to 50 parts by weight based on 100 parts by weight of the ink composition. The content of water and organic solvent depends on various factors, for example viscosity, surface tension, and drying speed of the ink composition. The content may also vary depending on a printing method and type of a substrate on which the ink is printed.

Examples of the organic solvent mainly used in the aqueous medium include alcohol such as methyl alcohol, ethyl alcohol, n-propyl alcohol, isopropyl alcohol, n-butyl alcohol, sec-butyl alcohol, t-butyl alcohol, and isobutyl alcohol; ketones such as acetone, methylethyl ketone, and diacetone alcohol; ester such as ethyl acetate and ethyl lactate; polyhydric alcohol such as ethyleneglycol, diethyleneglycol, triethyleneglycol, propyleneglycol, butyleneglycol, 1,4-butanediol, 1,2,4-butanetriol, 1,5-pentanediol, 1,2,6-hexanetriol, hexyleneglycol, glycerol, glycerol ethoxylate, and trimethylolpropane ethoxylate; lower alkyl ether such as ethyleneglycol monomethyl ether, ethyleneglycol monoethyl ether, diethyleneglycol methyl ether, diethyleneglycol ethyl ether, triethyleneglycol monomethyl ether, and triethyleneglycol monoethyl ether; nitrogen-containing compound such as 2-pyrrolidone and N-methyl-2-pyrrolidone; and sulfur-containing compound such as dimethyl sulfoxide, tetramethylenesulfone and thioglycol.

The ink composition of an embodiment of the present invention may further comprise an additive such as a viscosity modifier, a surfactant, a storage stabilizer, a wetting agent and a metal oxide.

The viscosity modifier acts to modify viscosity in order to maintain a smooth jetting of the ink. Examples of the viscosity modifier include casein and carboxymethylcellulose. The viscosity modifier is added to the ink composition in an amount of 0.1 to 5.0 parts by weight based on 100 parts by weight of the ink composition.

The surfactant acts to stabilize the jetting performance of the ink from a nozzle by adjusting the surface tension of the ink composition. An anionic or a non-ionic surfactant may be used.

Examples of the anionic surfactant include an alkylcarboxylic acid salt of 1–1,000 carbon atoms and preferably 10–200 carbon atoms, an alcohol sulfonic acid ester salt of 1–1,000 carbon atoms and preferably 10–200 carbon atoms, an alkylsulfonic acid salt of 1–1,000 carbon atoms and preferably 10–200 carbon atoms, an alkylbenzenesulfonic acid salt of 1–1,000 carbon atoms and preferably 10–200 carbon atoms and a mixture thereof. Examples of the non-ionic surfactant include polyoxyethylene alkyl ether wherein the alkyl moiety has 1–1,000 carbon atoms and preferably, 10–200 carbon atoms, polyoxyethylene alkyl phenyl ether wherein the alkyl moiety has 1–1,000 carbon atoms and preferably, 10–200 carbon atoms, polyoxyethylene secondary alcohol ether, polyoxyethylene-oxypropylene blockcopolymer, polyglycerine fatty acid ester, sorbitan fatty acid ester, and a mixture thereof. The surfactant is added to the ink composition in an amount of 0.1 to 5 parts by weight based on 100 parts by weight of the ink composition.

The wetting agent is used to prevent clogging of a nozzle. Examples of the wetting agent include polyhydric alcohol such as glycerine, ethylene glycol, diethylene glycol, triethylene glycol, propylene glycol, dipropylene glycol, hexylene glycol, 1,3-butanediol, 1,4-butanediol, 1,5-pentanediol, 2-buten-1,4-diol, 2-methyl-2-pentanediol and a mixture thereof. The wetting agent is added to the ink composition in an amount of 5 to 40 parts by weight based on 100 parts by weight of the ink composition.

The ink composition of an embodiment of the present invention may be prepared using the components as mentioned the above as the following procedure.

First, a water-soluble, antimicrobial active polymer, a colorant, a dispersing agent, a viscosity modifier and a surfactant are mixed while stirring in an aqueous medium to obtain a homogeneous mixture. Then, the mixture is filtered through a filter of a pore size of 0.45 to 1.0 μm to prepare the ink composition of the present invention.

Hereinafter, the present invention will be described with reference to the following examples and experiments but is not limited thereto.

EXAMPLE 1

Preparation of Water-Soluble, Antimicrobial Active Polymer 300 ml of dimethylsulfoxide (DMSO, JUNSEI CO.) as a solvent was poured into a rounded bottom flask. 22 g of 3-aminoproply triethoxysilane (ALDRICH CO.) and 16 g of adipic acid (ALDRICH CO.) were added to the flask and mixed. The flask was then heated at 120° C. under a nitrogen atmosphere for 8 hours. Then, 43 g of polyvinylalcohol of degree of polymerization of 300–500 (PVA, average Mw: 13,000–23,000, ALDRICH CO.) was added and heated at 80° C. Then, the DMSO was added until the PVA was completely dissolved. When the PVA was completely dissolved, the mixture was heated at 110° C. under a nitrogen atmosphere for 6 hours. The resultant mixture was cooled to room temperature, precipitated in excess methanol, and filtered. The filtrate was dried to yield a 35 g of a water-soluble, antimicrobial active polymer.

EXAMPLE 2

Preparation of Water-Soluble, Antimicrobial Active Polymer

A water-soluble, antimicrobial active polymer was prepared in the same manner as in Example 1 except that 16 g of phthalic anhydride (ALDRICH CO.) was used instead of adipic acid. The water-soluble, antimicrobial active polymer yielded 33 g.

EXAMPLE 3

Preparation of Water-Soluble, Antimicrobial Active Polymer

A water-soluble, antimicrobial active polymer was prepared in the same manner as in Example 1 except that 22 g of trimethoxysilane (ALDRICH CO.) was used instead of 3-aminopropyltriethoxysilane. The water-soluble, antimicrobial active polymer yielded 31 g.

EXAMPLE 4

Preparation of Water-Soluble, Antimicrobial Active Polymer

A water-soluble, antimicrobial active polymer was prepared in the same manner as in Example 3 except that 16 g of phthalic anhydride was used instead of adipic acid. The water-soluble, antimicrobial active polymer yielded 32 g.

EXAMPLE 5

Preparation of Ink Composition

| Component | Content |
| --- | --- |
| C. I. Direct Black 168 | 4.0 g |
| Water | 78 g |
| Isopropylalcohol | 3 g |

Water-soluble, Antimicrobial Active Polymer of Example 1 4.0 g

All the components were mixed and thoroughly stirred in a mechanical agitator for 30 minutes or more to obtain a homogeneous mixture. The resultant mixture was filtered through a filter with a pore size of approximately 0.45 μm to obtain a desired ink composition.

EXAMPLE 6

An ink composition was prepared in the same manner as in Example 5 except that C. I. Pigment Red 177 was used instead of C. I. Direct Black 168 and water-soluble, antimicrobial active polymer of Example 2 instead of Example 1 and a filter with a pore size of approximately 1.0 μm instead of approximately 0.45 μm.

EXAMPLE 7

An ink composition was prepared in the same manner as in Example 5 except that C. I. Direct Black 51 was used instead of C. I. Direct Black 168 and water-soluble, antimicrobial active polymer of Example 3 instead of Example 1.

EXAMPLE 8

An ink composition was prepared in the same manner as in Example 5 except that the water-soluble, antimicrobial active polymer of Example 4 was used instead of Example 1.

COMPARATIVE EXAMPLE 1

An ink composition was prepared in the same manner as in Example 5 except that polyvinylalcohol of degree of polymerization of 300–500 (PVA, ALDRICH CO.) was used instead of the water-soluble, antimicrobial active polymer of Example 1 and adding 0.1 g of 1,2-benzisothiazolin-3-one (BIT) as an antimicrobial agent.

COMPARATIVE EXAMPLE 2

An ink composition was prepared in the same manner as in Example 5 except that polyvinylalcohol of degree of polymerization of 300–500 (PVA, ALDRICH CO.) was used instead of the water-soluble, antimicrobial active polymer of Example 1, C. I. Pigment Red 177 instead of C. I. Direct Black 168 and a filter with a pore size of approximately 1.0 μm instead of approximately 0.45 μm and adding 0.1 g of 1,2-benzisothiazolin-3-one (BIT) as an antimicrobial agent.

COMPARATIVE EXAMPLE 3

An ink composition was prepared in the same manner as in Example 5 except that polyvinylalcohol of degree of polymerization of 300–500 (PVA, ALDRICH CO.) was used instead of the water-soluble, antimicrobial active polymer of Example 1 and C. I. Direct Black 51 instead of C. I. Direct Black 168 and adding 0.1 g of 1,2-benzisothiazolin-3-one (BIT) as an antimicrobial agent.

COMPARATIVE EXAMPLE 4

An ink composition was prepared in the same manner as in Example 5 except for using polyvinylalcohol of degree of polymerization of 300–500 (PVA, ALDRICH CO.) instead of the water-soluble, antimicrobial active polymer of Example 1 and C. I. Direct Black 51 instead of C. I. Direct Black 168 and adding 0.1 g of 1,2-benzisothiazolin-3-one (BIT) as an antimicrobial agent.

Properties of ink compositions of Examples 5–8 and Comparative examples 1–4 were measured according to the following method.

EXPERIMENT 1

Extended Storage Stability 100 ml of each ink composition of Examples 5–8 and Comparative Examples 1–4 was placed in a thermostable glass bottle, sealed, and deposited in a 60° C. thermostatic bath. After two months, the presence of a precipitate was observed and the results are presented in Table 1 below.

TABLE 1

|  | Example 5 | Example 6 | Example 7 | Example 8 | Comparative 1 | Comparative 2 | Comparative 3 | Comparative 4 |
|---|---|---|---|---|---|---|---|---|
| Storage stability | ○ | ○ | ○ | ○ | Δ | X | Δ | X |

Comparative: Comparative example
○: no precipitates, Δ: fine precipitates, X: coarse precipitates

EXPERIMENT 2

Antimicrobial Activity

*Salmonella* TA98 was added to each ink composition of Examples 5–8 and Comparative examples 1–4 and kept in a dark room at 37° C. for 48 hours. The number of colonies was calculated and the results are presented in Table 2 below.

TABLE 2

|  | Example 5 | Example 6 | Example 7 | Example 8 | Comparative 1 | Comparative 2 | Comparative 3 | Comparative 4 |
|---|---|---|---|---|---|---|---|---|
| Number of colonies | 78 | 83 | 81 | 85 | 132 | 125 | 115 | 121 |

Comparative: Comparative Example

As is apparent from the above description, unlike a conventional antimicrobial agent with strong toxicity and poor ink miscibility being separately added to ink compositions, the antimicrobial active polymer of the present invention is prepared by coupling an antimicrobial active compound to a branch of a conventional polymer used as a wetting agent or the like. As a result, the antimicrobial active polymer of the present invention provides excellent antimicrobial effect without affecting the properties of ink compositions comprising the polymer, in particular, the extended storage stability. In particular, because the antimicrobial active polymer has a lowered toxicity due to the coupling, droplets of ink compositions do not irritate the human skin. In addition, a printed picture also exhibits an antimicrobial effect for an extended duration.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A water-soluble, antimicrobial active polymer represented by Formula

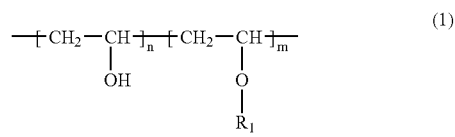

wherein:

n and m are the number of repeated units, n is 0.7–0.95 and m is 0.05–0.3 provided that n+m=1; and $R_1$ is a silane derivative represented by Formula 2:

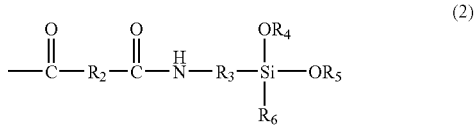

wherein:

$R_2$ is selected from the group consisting of an alkylene of 1–30 carbon atoms, a heteroalkylene of 1–30 carbon atoms, an arylene of 6–20 carbon atoms, an arylalkylene of 6–20 carbon atoms, a heteroarylene of 6–30 carbon atoms, and a heteroarylalkylene of 6–30 carbon atoms, each of which is unsubstituted or substituted with a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms;

$R_3$ is selected from the group consisting of an alkylene of 1–12 carbon atoms, an alkenylene or an alkynylene of 1–12 carbon atom, and an heteroalkylene of 1–12 carbon atoms, each of which is unsubstituted or substituted with a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms;

$R_4$ and $R_5$ are independently one of hydrogen, or an alkyl of 1–5 carbon atoms; and $R_6$ is one of a hydrogen, a hydroxyl, or an alkoxyl of 1–5 carbon atoms.

2. The water-soluble, antimicrobial active polymer according to claim 1, wherein the silane derivative of the Formula 2 is a compound represented by Formula 3:

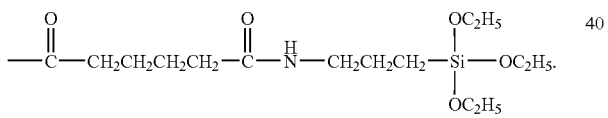
(3)

3. The water-soluble, antimicrobial active polymer according to claim 1, wherein the silane derivative of the Formula 2 is a compound represented by Formula 4:

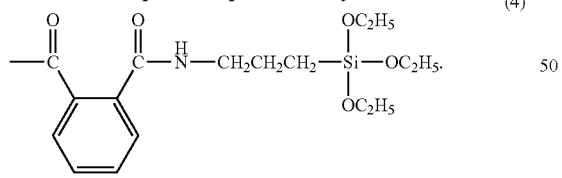
(4)

4. The water-soluble, antimicrobial active polymer according to claim 1, wherein the silane derivative of the Formula 2 is a compound represented by Formula 5:

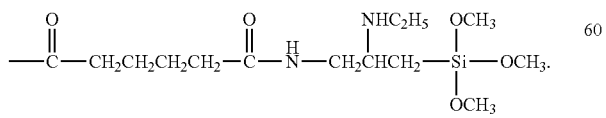
(5)

5. The water-soluble, antimicrobial active polymer according to claim 1, wherein the silane derivative of the Formula 2 is a compound represented by Formula 6:

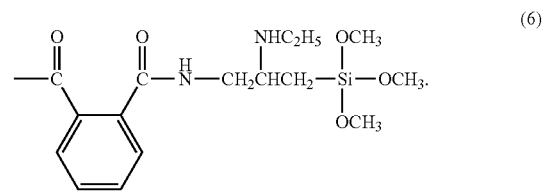
(6)

6. An ink composition comprising:

a water-soluble, antimicrobial active polymer represented by Formula 1:

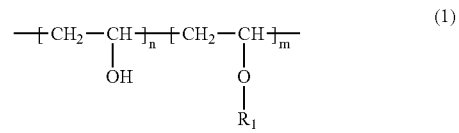
(1)

wherein:

n and m are the number of repeated units, n is 0.7–0.95 and m is 0.05–0.3 provided that n+m=1; and $R_1$ is a silane derivative represented by Formula 2:

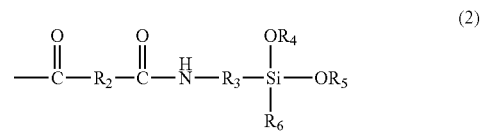
(2)

wherein:

$R_2$ is selected from the group consisting of an alkylene of 1–30 carbon atoms, a heteroalkylene of 1–30 carbon atoms, an arylene of 6–20 carbon atoms, an arylalkylene of 6–20 carbon atoms, a heteroarylene of 6–30 carbon atoms, and a heteroarylalkylene of 6–30 carbon atoms, each of which is unsubstituted or substituted with a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms;

$R_3$ is selected from the group consisting of an alkylene of 1–12 carbon atoms, an alkenylene or an alkynylene of 1–12 carbon atom, and an heteroalkylene of 1–12 carbon atoms, each of which is unsubstituted or substituted with a halogen, a hydroxyl, a nitro, a cyano, an amino, an amidino, a hydrazine, a hydrazone, carboxylic acid or a salt thereof, sulfonic acid or a salt thereof, phosphoric acid or a salt thereof, an alkyl of 1–20 carbon atoms, an alkenyl, an alkynyl, a heteroalkyl of 2–20 carbon atoms, an aryl of 6–20 carbon atoms, an arylalkyl of 6–30 carbon atoms, a heteroaryl of 6–30 carbon atoms, or a heteroarylalkyl of 6–30 carbon atoms;

$R_4$ and $R_5$ are independently one of hydrogen, or an alkyl of 1–5 carbon atoms; and $R_6$ is one of a hydrogen, a hydroxyl, or an alkoxyl of 1–5 carbon atoms;

a colorant; and an aqueous medium.

7. The ink composition according to claim 6, wherein the water-soluble, antimicrobial active polymer is added to the ink composition in an amount of 1 to 10 parts by weight based on 100 parts by weight of the ink composition.

8. The ink composition according to claim 6, wherein the aqueous medium is one of water alone or water in combination with at least one organic solvent.

9. The ink composition according to claim 8, wherein the organic solvent comprises at least one of: a non-polyhydric alcohol, a ketone, an ester, a polyhydric alcohol, a lower alkyl ether, a nitrogen-containing compound, or a sulfur-containing compound.

10. The ink composition according to claim 9, wherein the non-polyhydric alcohol is at least one alcohol selected from the group consisting of methyl alcohol, ethyl alcohol, n-propyl alcohol, isopropyl alcohol, n-butyl alcohol, sec-butyl alcohol, t-butyl alcohol, and isobutyl alcohol.

11. The ink composition according to claim 9, wherein the ketone is at least one ketone selected from the group consisting of acetone, methylethyl ketone, and diacetone alcohol.

12. The ink composition according to claim 9, wherein the ester is at least one ester selected from the group consisting of ethyl acetate and ethyl lactate.

13. The ink composition according to claim 9, wherein the polyhydric alcohol is at least one polyhedric alcohol selected from the group consisting of ethyleneglycol, diethyleneglycol, triethyleneglycol, propyleneglycol, butyleneglycol, 1,4-butanediol, 1,2,4-butanetriol, 1,5-pentanediol, 1,2,6-hexanetriol, hexyleneglycol, glycerol, glycerol ethoxylate, and trimethylolpropane ethoxylate.

14. The ink composition according to claim 9, wherein the lower alkyl ether is at least one lower alkyl ether selected from the group consisting of ethyleneglycol monomethyl ether, ethyleneg lycol monoethyl ether, d iethyleneg lycol methyl ether, diethyleneglycol ethyl ether, triethyleneglycol monomethyl ether, and triethyleneglycol monoethyl ether.

15. The ink composition according to claim 9, wherein the nitrogen-containing compound is at least one nitrogen-containing compound selected from the group consisting of 2-pyrrolidone and N-methyl-2-pyrrolidon.

16. The ink composition according to claim 9, wherein the sulfur-containing compound is at least one sulfur-containing compound selected from the group consisting of dimethyl sulfoxide, tetramethylenesulfone and thioglycol.

17. The ink composition according to claim 6, further comprising a viscosity modifier, a surfactant, a storage stabilizer and a wetting agent.

18. An ink composition comprising:
a water-soluble, antimicrobial active polymer represented by Formula 1:

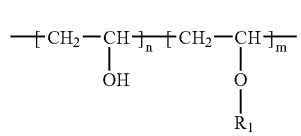

wherein:
n and m are the number of repeated units, n is 0.7–0.95 and m is 0.05–0.3 provided that n+m=1; and
$R_1$ is a silane derivative represented by Formula 3:

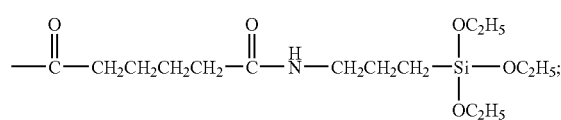

a colorant; and
an aqueous medium.

19. An ink composition comprising:
a water-soluble, antimicrobial active polymer represented by Formula 1:

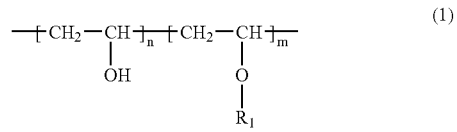

wherein:
n and m are the number of repeated units, n is 0.7–0.95 and m is 0.05–0.3 provided that n+m=1; and
$R_1$ is a silane derivative represented by Formula 4:

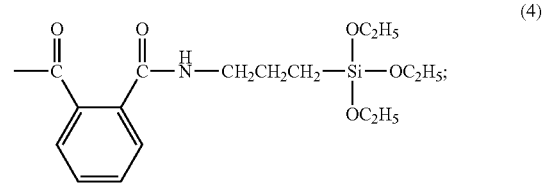

a colorant; and
an aqueous medium.

20. An ink composition comprising:
a water-soluble, antimicrobial active polymer represented by Formula 1:

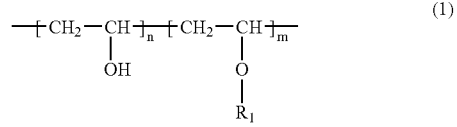

wherein:
n and m are the number of repeated units, n is 0.7–0.95 and m is 0.05–0.3 provided that n+m=1; and
$R_1$ is a silane derivative represented by Formula 3:

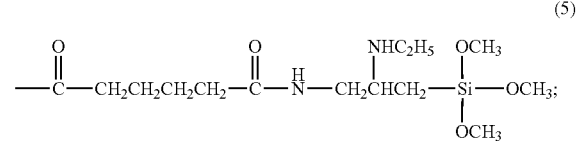

a colorant; and
an aqueous medium.

21. An ink composition comprising:
a water-soluble, antimicrobial active polymer represented by Formula 1:
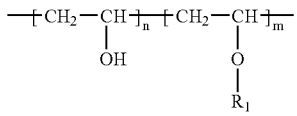
(1)
wherein:
n and m are the number of repeated units, n is 0.7–0.95 and m is 0.05–0.3 provided that n+m=1; and
$R_1$ is a silane derivative represented by Formula 6:
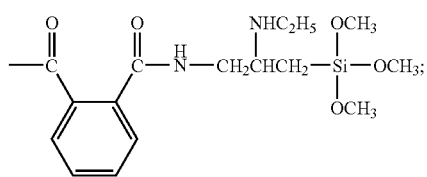
(6)
a colorant; and
an aqueous medium.
* * * * *

UNITED STATES PATENT AND TRADEMARK OFFICE
CERTIFICATE OF CORRECTION

PATENT NO.       : 7,112,630 B2
APPLICATION NO.  : 10/647144
DATED            : September 26, 2006
INVENTOR(S)      : Kyung-hoon Lee et al.

It is certified that error appears in the above-identified patent and that said Letters Patent is hereby corrected as shown below:

Col. 10, line 23, after "Formula" insert --1:--

Col. 11, line 18, change "carbon atom" to --carbon atoms--

Col. 11, line 31, after "hydrogen" delete ","

Col. 12, line 52, change "carbon atom" to --carbon atoms--

Col. 12, line 62, after "hydrogen" delete ","

Col. 13, line 26, change "polyhedric" to --polyhydric--

Col. 13, line 35, change "ethyleneg lycol" to --ethyleneglycol--

Col. 13, line 35, change "d iethyleneg lycol" to --diethyleneglycol--

Signed and Sealed this

Twentieth Day of February, 2007

JON W. DUDAS
*Director of the United States Patent and Trademark Office*